(12) United States Patent
Popovic et al.

(10) Patent No.: US 10,342,426 B2
(45) Date of Patent: *Jul. 9, 2019

(54) WIRELESS IMPLANTABLE DATA COMMUNICATION SYSTEM, METHOD AND SENSING DEVICE

(71) Applicant: MyndTec Inc., Mississauga (CA)

(72) Inventors: Milos R. Popovic, Mississauga (CA); Massimo Tarulli, Toronto (CA); Aleksandar Prodic, Toronto (CA); Santa Concepcion Huerta Olivares, San Diego, CA (US)

(73) Assignee: MyndTec Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/823,121

(22) Filed: Nov. 27, 2017

(65) Prior Publication Data

US 2018/0078137 A1 Mar. 22, 2018

Related U.S. Application Data

(63) Continuation of application No. 14/390,160, filed as application No. PCT/CA2013/000222 on Mar. 15, 2013, now Pat. No. 9,861,282.
(Continued)

(51) Int. Cl.
*A61B 5/00* (2006.01)
*A61B 5/04* (2006.01)
(Continued)

(52) U.S. Cl.
CPC .......... *A61B 5/0022* (2013.01); *A61B 5/0006* (2013.01); *A61B 5/0031* (2013.01);
(Continued)

(58) Field of Classification Search
CPC ... A61B 5/0031; A61B 5/0215; A61B 5/0028; A61B 2560/0214; A61B 2560/0219;
(Continued)

(56) References Cited

U.S. PATENT DOCUMENTS

| | | | |
|---|---|---|---|
| 2006/0084380 A1* | 4/2006 | Hoyt ................... | H04B 5/02 455/41.1 |
| 2007/0088221 A1* | 4/2007 | Stahmann ............ | A61B 5/0205 600/485 |

(Continued)

OTHER PUBLICATIONS

An et al., Design for a simplified cochlear implant system, IEEE Trans Biomed Eng (2007), 54(6):973-982.
(Continued)

*Primary Examiner* — Golam Sorowar
(74) *Attorney, Agent, or Firm* — Bret E. Field; Bozicevic, Field & Francis LLP

(57) ABSTRACT

Disclosed herein is a wireless implantable communication system, method and sensing device, wherein an implantable data conversion module is adapted for operative coupling to a distinct or integrated implantable sensing device for the conversion of a characteristic signal for transmission thereof to an external receiver, e.g. by way of an inductive element. Upon positioning an external inductive element in the vicinity of the implanted device, a corresponding signal is induced within the external element allowing for reconstruction of the converted signal, and thereby allowing for recovery of the characteristic signal. Embodiments for the communication of data across a biological barrier, including communications from an external transmitter to an implanted receiver, an implanted transmitter to an external receiver, and an implanted transmitter/receiver pair are also disclosed.

17 Claims, 5 Drawing Sheets

Related U.S. Application Data

(60) Provisional application No. 61/620,627, filed on Apr. 5, 2012.

(51) Int. Cl.

| | | |
|---|---|---|
| *A61F 2/08* | (2006.01) | |
| *A61F 2/72* | (2006.01) | |
| *A61N 1/05* | (2006.01) | |
| *A61N 1/36* | (2006.01) | |
| *G06F 3/01* | (2006.01) | |
| *H04B 5/00* | (2006.01) | |
| *A61M 5/172* | (2006.01) | |
| *A61N 1/372* | (2006.01) | |
| *A61B 5/1455* | (2006.01) | |

(52) U.S. Cl.
CPC ........ *A61B 5/14552* (2013.01); *A61B 5/7225* (2013.01); *A61F 2/08* (2013.01); *A61F 2/72* (2013.01); *A61M 5/172* (2013.01); *A61N 1/3606* (2013.01); *A61N 1/36036* (2017.08); *A61N 1/37217* (2013.01); *G06F 3/015* (2013.01); *A61B 5/04* (2013.01); *A61F 2002/0894* (2013.01); *A61N 1/0534* (2013.01); *A61N 1/36064* (2013.01); *A61N 1/36067* (2013.01); *A61N 1/36082* (2013.01); *A61N 1/36125* (2013.01); *A61N 1/37223* (2013.01); *H04B 5/0031* (2013.01); *H04B 5/0037* (2013.01); *H04B 5/0081* (2013.01)

(58) Field of Classification Search
CPC .......... A61B 2562/0247; A61B 5/0006; A61B 5/0017; A61B 5/0024; A61B 5/0205; A61B 5/04001; A61B 5/053; A61N 1/37217; A61N 1/3727; A61N 1/37288; A61N 1/362; A61N 1/3627; A61N 1/36564; A61N 1/3706; H04B 13/005; H04B 5/0031; H04B 5/0043; H04B 5/0075; H04B 5/0093; H04B 5/02

See application file for complete search history.

(56) References Cited

U.S. PATENT DOCUMENTS

| | | | |
|---|---|---|---|
| 2007/0239229 A1* | 10/2007 | Masoud | A61B 5/0024 607/60 |
| 2009/0043361 A1* | 2/2009 | Baumgartner | A61N 1/37211 607/60 |
| 2010/0106041 A1* | 4/2010 | Ghovanloo | A61B 5/0006 600/544 |
| 2010/0114189 A1* | 5/2010 | Donofrio | A61N 1/36114 607/2 |
| 2010/0114209 A1* | 5/2010 | Krause | A61N 1/37217 607/5 |
| 2010/0246872 A1* | 9/2010 | Ochoco | H04R 25/556 381/328 |
| 2010/0249882 A1* | 9/2010 | Houben | A61N 1/37217 607/60 |
| 2012/0041310 A1* | 2/2012 | Towe | A61B 5/0028 600/437 |
| 2012/0078322 A1 | 3/2012 | Dal Molin et al. | |
| 2012/0197350 A1* | 8/2012 | Roberts | A61B 5/0028 607/60 |

OTHER PUBLICATIONS

Chestek et al., HermesC: RF Wireless Low-Power Neural Recording System for Freely Behaving Primates, Circuits and Systems 2008. ISCAS 2008. IEEE International Symposium on May 18-21, 2008, p. 1752-1755.

Liang et al., An implantable bi-directional wireless transmission system for transcutaneous biological signal recording, Physiol Meas (2005), 26(1):83-97.

Mohseni et al., Wireless Multichannel Biopotential Recording Using an Integrated FM Telemetry Circuit, Proceedings of the 26th Annual International Conference of the IEEE EMBS San Francisco, CA, USA • Sep. 1-5, 2004, p. 4083-4086.

Mojarradi et al., A Miniaturized Neuroprosthesis Suitable for Implantation Into the Brain, IEEE Transactions on Neural Systems and Rehabilitation Engineering (2003), 11(1): 38-42.

Rizk et al., A single-chip signal processing and telemetry engine for an implantable 96-channel neural data acquisition system, J Neural Eng (2007), 4(3):309-321.

Song et al., Active Microelectronic Neurosensor Arrays for Implantable Brain Communication Interfaces, IEEE Transactions on Neural Systems and Rehabilitation Engineering (2009), 17(4):339-345.

* cited by examiner

WIRELESS IMPLANTABLE DATA COMMUNICATION SYSTEM, METHOD AND SENSING DEVICE

CROSS-REFERENCE TO RELATED APPLICATIONS

This application is a continuation application of U.S. patent application Ser. No. 14/390,160 filed Oct. 2, 2014, issued on Jan. 9, 2018 as U.S. Pat. No. 9,861,282, which is a national phase application under 35 U.S.C. § 371 of PCT Patent Application No. PCT/CA2013/000222 filed Mar. 15, 2013, which claims the benefit of priority to U.S. Provisional Patent Application No. 61/620,627 filed Apr. 5, 2012, all the contents of which are herein incorporated by reference into the Detailed Description, herein below.

FIELD OF THE DISCLOSURE

The present disclosure relates to implantable devices, and in particular, to a wireless implantable data communication system, method and sensing device.

BACKGROUND

The prospect of providing wireless implantable devices for the purpose of medical treatment, rehabilitation, monitoring and/or diagnostics is an attractive one, whereby locally targeted devices can provide significant benefits over externally implemented alternatives. However, while implantation in itself can pose a series of challenges, whether in the process of implanting the device or in providing manufacturing materials that will not adversely affect the condition of the subject, other challenges are also imminent. Namely, most implantable devices will be battery powered and therefor, if the device is to have a sufficiently long lifespan, highly efficient circuitry or adequate battery recharging applications can become particularly relevant. Furthermore, communication of information to and from the implanted device may be of particular importance depending on the application at hand, while traditional communication techniques and components may not be readily amenable to implantation, or appropriate in such contexts. Namely, while a number of examples are available for the provision of wireless data communications, for example as provided by Sharma et al. in U.S. Pat. No. 5,615,229 to a Short Range Inductively Coupled Communication System Employing Time Variant Modulation, these and other such examples do not contemplate the limitations and constraints applied to implantable devices, nor do they contemplate the particular conditions in which implantable devices are designed to operate, and media through which signals communicated thereby or thereto are subjected to.

Also, as will be appreciated by the person of ordinary skill in the art, communicating data from an external device to an implanted device, for example as described in U.S. Pat. No. 6,671,559 to Goldsmith et al. for a Transcanal, Transtympanic Cochlear Implant System for the Rehabilitation of Deafness and Tinnitus, wherein acoustic data is communicated via magnetic inductive coupling to the implanted device for the purpose of stimulating the inner ear, does not generally pose as significant challenges with respect to power consumption efficiency. Namely, the internal reception of externally transmitted data can generally be much more straightforward in implementation than the reverse. It will be appreciated that other challenges and limitations associated with implanted device communications may be of particular relevance depending on the application at hand, and that while power consumption and conservation may be highlighted to some extent herein, other aspects of implantable device communications may also be considered pertinent in the present discussion.

In other examples, an implanted battery-operated device can be inductively recharged via an external device. For example, energy can be transferred transcutaneously via magnetic induction between an external charger and implanted device, such as described in U.S. Pat. No. 5,713,939 to Nedugadi et al. for a Data Communication System for Control of Transcutaneous Energy Transmission to an Implantable Medical Device and U.S. Pat. No. 6,772,011 to Dolgin for Transmission of Information from an Implanted Medical Device. In these examples, internal control or feedback data relative to the battery charging process is transmitted for external reception via the same magnetic induction elements used in the charging process. While internally generated, such simple feedback signals are effectively powered by the charging process and therefor of little consequence to the normal operation of the implanted device.

In U.S. Patent Application Publication No. 2007/0167867 to Wolf for a System for Transcutaneous Monitoring of Intracranial Pressure, an implantable sensor module measures and communicates an intracranial pressure to an external module via, in one embodiment, a near infrared (NIR) beam that traverses biological tissue for the digital transmission of data, wherein the sensor module, rather than being battery-powered, is externally powered via inductive coupling with the exterior module. Alternatively, the sensing module is provided with pressure sensing circuits having a pressure-variable resonance, wherein an external circuit is configured to excite and detect a resonant frequency of the internal circuit(s) and thereby ascertain an intracranial pressure. Once again, while information is being relayed from the implanted device, the sensing module in these examples is effectively powered via external means.

Another example making use of optical communication means is provided in Active Microelectronic Neurosensor Arrays for Implantable Brain Communication Interfaces to Song et al. (IEEE Trans Neural Syst Rehabil Eng. 2009 August, 17(4), 339-345). In this example, the wireless transmission of implanted neurosensor array data is implemented via an integrated semiconductor diode laser, wherein the implanted device is powered via inductive or optical coupling.

An alternative approach relies rather on radio frequency (RF) transmissions, for example implemented via various frequency modulated (FM) transmission schemes or the like readily known in the art. Some examples applying this approach may be found in the following: A miniaturized Neuroprosthesis Suitable for Implantation into the Brain to Mojarradi et al. (IEEE Transactions on Neural Systems and Rehabilitation Engineering, Vol. 11, No. 1, March 2003); Wireless Multichannel Biopotential Recording Using an Integrated FM Telemetry Circuit to Mohseni (IEEE Transaction on Neural Systems and Rehabilitation Engineering, Vol. 13, No. 3, September 2005); A Single-Chip Signal Processing and Telemetry Engine for an Implantable 96-Channel Neural Data Acquisition System to Rizk et al. (J. Neural Eng. 4 (2007) 309-321); HermesC: RF Wireless Low-Power Neural Recording System for Freely Behaving Primates to Chestek et al. (Proceedings of the 2008 IEEE International Symposium on Circuits and Systems (ISCAS2008), Seattle, Wash. 2008, p. 1752-1755); International Application Publication No. WO2007/061654 to Kenergy, Inc.

Another such example is provided by US Patent Application No. 2010/0106041 to Ghovanloo et al. for Systems and Methods for Multichannel Wireless Implantable Neural Recording. In this example, an implantable system is provided wherein a neural signal from each of a number of data channels are converted to a pulse-width-modulated time-division-multiplexed signal that is ultimately transmitted via an RF transmitter (e.g. FM/FSK signal) for reception and reconstruction by an external device.

While the above introduce some prospects in the provision of wireless communications between implanted and externally disposed devices, such provisions are generally limited either in the complexity of the data being communicated (i.e. feedback/control data), by the complexity of the communication scheme (e.g. RF technologies) and associated drawbacks (power consumption, implanted circuit complexity, compliance with different wireless communication regulations, etc.). Furthermore, while optical communication schemes may be applicable in some circumstances, they may pose certain difficulties for certain applications, as will be readily appreciated by one of ordinary skill in the art.

Therefore, there remains a need for a wireless implantable data communication system, method and sensing device that overcomes some of the drawbacks of known technologies, or at least, provides the public with a useful alternative.

This background information is provided to reveal information believed by the applicant to be of possible relevance to the present invention. No admission is necessarily intended, nor should be construed, that any of the preceding information constitutes prior art against the present invention.

SUMMARY

An object of the invention is to provide a wireless implantable data communication system, method and sensing device. In accordance with an embodiment of the invention, there is provided a system for monitoring an internal characteristic of a body, the system comprising: an implantable device suitable for implantation in the body and comprising a sensing device for generating a characteristic signal representative of the internal characteristic, a signal conversion module operatively coupled to said sensing device for converting said characteristic signal into an encoded signal defined by successive width-encoded pulses representative of said characteristic signal; and an inductor operatively coupled to said signal conversion module for propagation therethrough of said encoded signal; and an external receiving device comprising an external inductor for disposal at a distance from said implantable inductor for operative magnetic coupling thereto, wherein each rise and fall of said successive width-encoded pulses induces corresponding signal pulses through said external inductor, said external receiving device adapted for operative coupling to a signal reconstruction module for reconstructing each said rise and fall of said encoded signal from said corresponding signal pulses to recover said characteristic signal and thereby monitor the internal characteristic.

In accordance with another embodiment of the invention, there is provided a method for sensing an internal characteristic of a body, the method comprising the steps of: internally generating an encoded signal defined by successive width-encoded pulses representative of the internal characteristic; for each rise and fall in said encoded signal, magnetically inducing corresponding external signal pulses; and externally reconstructing each said rise and fall of said encoded signal from said corresponding signal pulses, thereby recovering said internally generated characteristic signal.

In accordance with another embodiment of the invention, there is provided a system for monitoring an internal characteristic of a body, the system comprising: an implantable device suitable for implantation in the body and comprising a sensing device for generating a characteristic signal representative of the internal characteristic, an analog signal modulation module operatively coupled to said sensing device for modulating said characteristic signal into an analog transmission signal, and an implantable inductor operatively coupled to said analog signal modulation module for propagation therethrough of said analog transmission signal; and an external receiving device comprising an external inductor for disposal at a distance from said implantable inductor for operative magnetic coupling thereto, wherein propagation of said analog transmission signal through said implantable inductor induces a corresponding analog signal through said external inductor, said external receiving device further comprising a signal reconstruction module for reconstructing said analog transmission signal from said corresponding signal to recover said characteristic signal.

In accordance with another embodiment of the invention, there is provided a system for communicating intra-body signals generated by an implantable sensing device, the system comprising: an implantable analog signal modulation device adapted for operative coupling to the implantable sensing device for modulating intra-body signals generated thereby into an analog transmission signal; an implantable inductor operatively coupled to said modulation device for propagation therethrough of said analog transmission signal; and an external receiving device comprising an external inductor for disposal at a distance from said implantable inductor for operative magnetic coupling thereto, wherein propagation of said analog transmission signal through said implantable inductor induces a corresponding analog signal through said external inductor, said external receiving device further comprising a signal reconstruction module for reconstructing said analog transmission signal from said corresponding signal to recover the intra-body signals.

In accordance with another embodiment of the invention, there is provided a system for communicating data across a biological barrier, the system comprising: an encoder for generating an encoded signal defined by successive width-encoded pulses representative of the data; a transmission inductor operatively coupled to said encoder for propagation therethrough of said encoded signal; a receiver comprising a receiving inductor for disposal at a distance through the biological barrier from said transmission inductor for operative magnetic coupling thereto, wherein each rise and fall of said successive width-encoded pulses induces corresponding signal pulses through said receiving inductor; and a data reconstruction module for reconstructing each said rise and fall of said encoded signal from said corresponding signal pulses to recover said encoded signal.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

DETAILED DESCRIPTION

Figure 1:
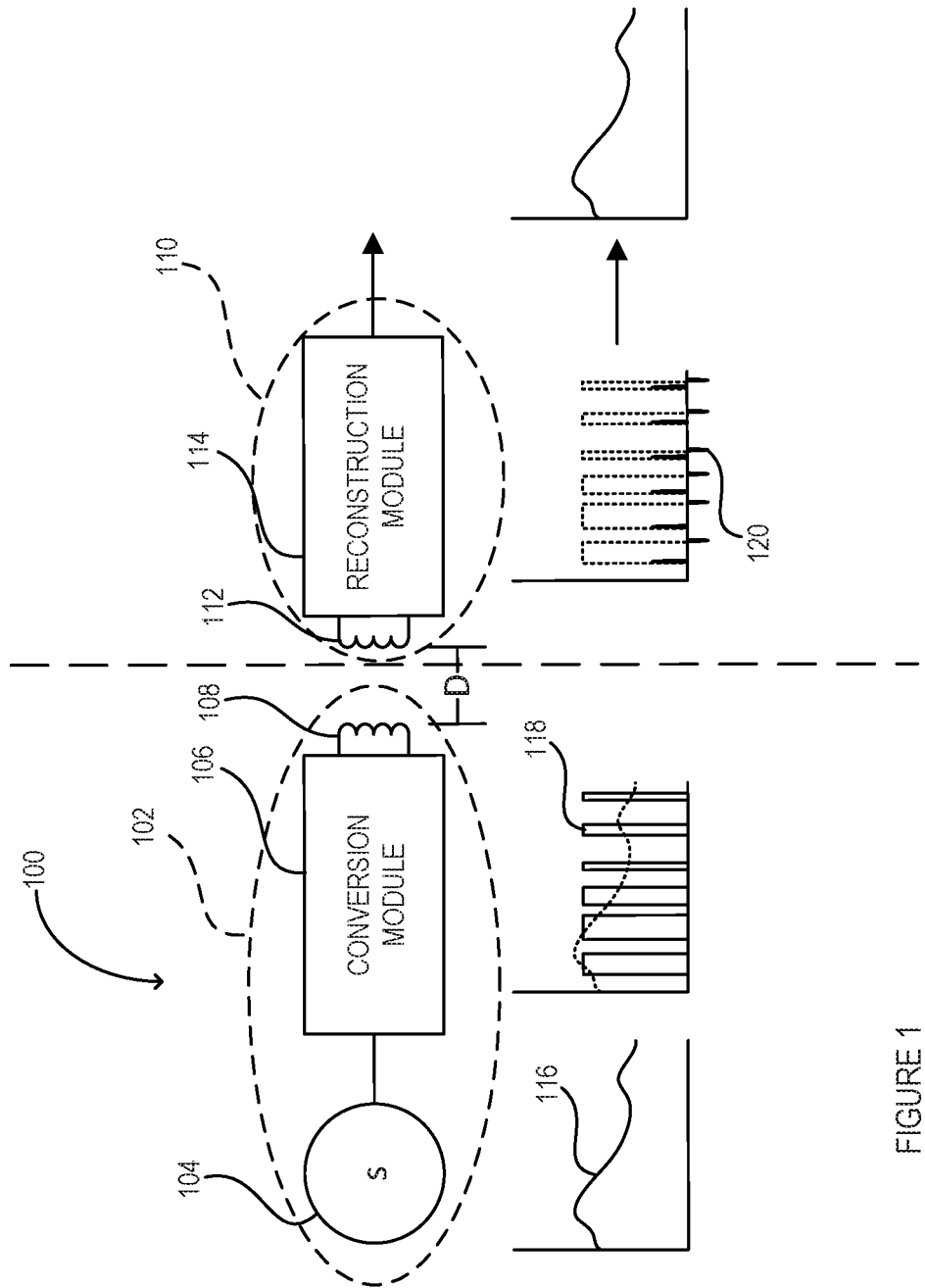
FIG. 1 is a schematic diagram of an implantable communication system, in accordance with one embodiment of the invention.

The embodiments of the invention, as described herein, relate generally to the transfer of data across a biological barrier, be it data representative of one or more internal characteristics of a body to be communicated outside the body, external data to be communicated to an implanted device within the body, or again data to be communicated between implanted devices, for example. In general, the body providing the biological barrier will consist of a live or dead human or animal body. In the context of data being communicated from within the body, transferred signals, generally referred to herein as "intra-body signals" are meant to include different signals representative of a condition, characteristic and/or parameter, directly or indirectly sensed or otherwise observed from within the body. In some examples, intra-body signals may include "biosignals", which are meant to include different signals representative of a sensed biological/physiological condition, characteristic and/or parameter, directly or indirectly sensed or otherwise observed from within the body. Such biosignals are described herein within the context of patient monitoring and/or diagnostics, however, it will be appreciated that embodiments of the invention described herein may be practiced for the transmission of data to be used for a variety of purposes or in a variety of contexts, which are therefore considered to fall within the scope of this disclosure. Similarly, different embodiments may also or alternatively consider the transfer of "environmental signals" meant to include different signals representative of an environmental condition, characteristic and/or parameter directly or indirectly sensed or otherwise observed from within the body, or again representative of an internal response of the body to such environmental conditions or characteristics. In yet other examples, such environmental signals may rather allow for a determination of the implanted body's position or movement. While focus will be provided below on embodiments for manipulating and communicating intra-body signals for external consumption, examples that rather consider the communication of external data to an implanted device, for example, will also be discussed in greater detail below, and are thus intended to fall within the general scope and nature of the present disclosure.

As will be described in greater detail below, some embodiments of the invention rely on an effective data signal communication design and system implemented by, in some embodiments, a concise implantable data manipulation and transmission circuit or platform useable for the transmission of a variety of intra-body signals, in one or more data channels, from within the body to an external receiver. Accordingly, it will be appreciated that while different examples are considered herein in the context of medical monitoring and/or diagnostics via the manipulation of generally electric biosignals, used for example in the context of an electrocardiogram (ECG), electroencephalogram (EEG), electrocorticogram (ECoG), electromyogram (EMG), electro-oculogram (EOG), electrogastrogram (EGG), etc., other types of signals may also be considered. For instance, upon adding a transducer in front or as part of the described systems, other non-electrical biological parameters such as blood pressure, body temperature, blood oxygen saturation ($SpO_2$), blood $CO_2$ saturation, NO concentration, respiration, and/or other types of physiological sensing systems, as will be readily appreciated by the skilled artisan, may be considered, whereby such sensed parameters are effectively converted by an appropriate implantable transducer or the like to generate an electrical signal representative thereof and readily transmittable using different embodiments of the invention, as described herein.

In other embodiments, environmental sensors are used instead of or in combination with biosensors, which environmental sensors may include, but are not limited to, gravitational sensors, magnetic field sensors, radiation sensors and the like. For instance, the implantation of such environmental sensors within the body may allow one to measure or evaluate a response of the body to such environmental conditions, detect an intensity or amplitude of environmental conditions within the body, or use such measurements to identify a position or movement of the body, for example. It will be appreciated by the skilled artisan in considering the following disclosure that other types of sensors and sensed characteristics may be considered herein without departing form the general scope and nature of the present disclosure.

As noted above, while the following primarily focuses on the description of embodiments where data is transferred across a biological barrier from within the body to an external receiver (e.g. for the transfer of data signals representative of an internal characteristic of the body), other embodiments are also considered herein wherein data is communicated across a biological barrier by way of an external transmitter to an implanted receiver, or again between an implanted transmitter/receiver pair. These and other such embodiments are considered to fall within the scope and nature of the present disclosure.

In accordance with some embodiments, a wireless implantable communication system, method and sensing device are described, wherein an implantable data conversion module is adapted for operative coupling to a distinct or integrated implantable sensing device for the conversion of a characteristic signal, representative of an internal characteristic of a body within which it is implanted, for transmission thereof to an external receiver. Namely, the conversion module is operatively coupled to an inductive element, such as an inductive coil or the like, whereby the converted signal is transmitted therethrough to generate a time-variable magnetic field in the vicinity of the inductor. Upon positioning an external inductive element in the vicinity of the implanted device, a corresponding signal is induced within the external element. Operative coupling of this external inductive element to a signal reconstruction module, as described below, allows for reconstruction of the converted signal from the induced signal, thereby allowing for recovery of the characteristic signal representative of the sensed internal parameter.

In accordance with some embodiments, the system herein described provides for the transfer of signal processing complexities from the implantable unit, where size and power are often particularly limited, to the external unit. Furthermore, as processing techniques and requirements evolve, the external unit may be modified and/or upgraded without altering operation of the implanted unit. Accordingly, while other solutions may require the implanted device to be replaced before expiry of its components, some of the solutions described herein allow generally for the reconstruction of the originating raw signal within the external unit, thereby allowing for an ongoing evolution of processing techniques and approaches while using the implanted device to the maximum of its intended lifespan.

Referring now to FIG. 1, a system, generally referred to using the numeral 100, and in accordance with an illustrative embodiment of the invention, will now be described. In this example, the system 100 comprises an implantable device 102 suitable for implantation in a body (e.g. via suitable encapsulation and/or manufacture using bio-acceptable materials and practices for implantation in a human or animal body, for example in a medical monitoring, diagnostic and/or rehabilitation context, etc.) and comprising, in this illustrative embodiment, an integrated sensing device 104 for generating a characteristic signal representative of an internal characteristic of the body. The implantable device 102 further comprises a signal conversion module 106 operatively coupled to the sensing device 104 for converting the characteristic signal for transmission via an inductor 108 (i.e. a transmission inductor) operatively coupled thereto.

The system 100 further comprises an external receiving device 110 comprising an external inductor 112 (i.e. a receiving inductor) for disposal at a distance (D) from the implantable inductor 108 for operative magnetic coupling thereto, such that, as the converted signal is propagated through the implantable inductor 108, a corresponding signal is inductively generated, over distance D, in the external inductor 112. In this particular embodiment, the external receiving device 110 comprises an integrated reconstruction module 114 adapted for operative coupling to the external inductor 112 to reconstruct the internally converted signal from the externally induced signal and thereby recover, through appropriate manipulation, the internally sensed signal.

In this particular embodiment, as depicted by the accompanying step-by-step signal manipulation charts of FIG. 1, the internally generated signal 116 is first converted by the conversion module 106 into an encoded signal representative of the characteristic signal. For example, and in accordance with one embodiment, the encoded signal may comprise successive width-encoded pulses, such as provided by a substantially square-wave signal or the like, whereby the respective width of each pulse is encoded to be representative of the intra-body signal. For instance, one such embodiment may employ pulse-width-modulation (PWM) or the like, as depicted by internally converted signal 118 with characteristic signal 116 shown overtop in dotted lines for illustrative purposes. Upon propagating the converted signal 118 through the internal inductor 108, a localized magnetic field variation is manifested through the body and across distance D to effectively induce a corresponding signal 120 in external inductor 112. Namely, each rise and fall of the converted signal 118 (depicted in dotted lines overtop corresponding signal 120 for illustrative purposes) induces corresponding signal pulses through the external inductor 112, which pulses can be used to reconstruct the internally converted signal, for example by identifying the start and end of each square pulse of the internally converted signal by its corresponding externally induced pulses, and ultimately recovering the characteristic signal of interest.

In this particular example, for instance, each rise and fall in the square wave signal induces corresponding positive and negative pulses, respectively, wherein each positive pulse is separated from its corresponding negative pulse by a substantially flat signal, thus facilitating identification of these pulses in reconstructing the transmitted signal. It will be appreciated that while relatively sharp pulses are illustratively induced in the present example, certain pulse identification methods may allow for the detection of broader induced pulses without significant loss of signal reconstruction precision or exactitude. For example, employing a hysteretic band to detect the onset of each induced pulse, as discussed in greater detail below, provided the receiver circuit is substantially identical for each induced pulse (e.g. for both positive and negative induced pulses in this example), and provided each pulse is separated by a substantially flat signal (e.g. comprising relatively low amplitude fluctuations), the thereby detected onset of each induced pulse may be effectively used in the reconstruction of the transmitted signal, irrespective of the induced pulses' duration. It will also be appreciated that while the above example relies on PWM to produce a substantially square wave signal encoding the intra-body signal, other signal shapes and pulse-width encoding schemes may be considered herein to produce a similar effect, without departing from the general scope and nature of the present disclosure. For example, while width-encoded square waves provide a readily workable option, other signal shapes that allow for the provision of width encoded pulses having relatively sharp rise and fall times may be considered herein to achieve similar results, whereby similarly induced pulses representative of these relatively sharp rise and fall times may be induced and identified to reconstruct the original signal. For example, different pulse profiles having relatively sharp rise and fall times may provide for adequate width-encoding within the present context, while exhibiting alternative peak profiles (e.g. rounded, spiked, random). Furthermore, it will be appreciated that while some embodiments may use the width of successive pulses to encode a given signal, width-encoded pulses may also be characterized by the spacing between signals and pulses to provide similar effects. These and other such considerations will be readily appreciated by the skilled artisan upon reading the following disclosure, and are therefore intended to fall within the scope of the present disclosure.

As will be appreciated by the person of ordinary skill in the art, the system 100 provides an example of a system allowing for the efficient communication of intra-body signals (e.g. data) from an implantable sensing device to an externally disposed receiver and downstream signal monitoring/diagnostic platform, via inductive coupling between the implantable and external devices across a biological boundary. Namely, the proposed system, when used in conjunction, for example, with a subdermal or subcutaneous sensing device, or again sensing devices implanted deeper within the body and operatively coupled to a shallower implanted conversion module and inductor, allows for the transmission of intra-body data such as biological/physiological and/or internal environmental data across the skin (or thicker biological boundary) without the provision of invasive wires or cabling. Unlike known optical systems that rely on transcutaneous optical transmissions, or complicated RF systems relying on FM data signals, embodiments of the invention herein described allow for the inductive transmission of analog signals across a biological boundary with limited internal data manipulation and relatively simple communication hardware (e.g. a single inductor such as a coreless inductive coil or the like), which translates, in some embodiments, into reduced implantable device circuitry and reduced required processing/transmission power. Other and/or alternative advantages and benefits will be readily apparent to the person of ordinary skill in the art, depending on the specifics of each particular embodiment. It will also be appreciated by the skilled artisan that while the following examples focus on the use of coreless inductive coils, which are currently known to provide greater biocompatibility and reduced side effects, the provision of a cored inductive coil may still be considered herein as a viable option in some embodiments, for example, where biocompatibility is of lesser concern, or again, where new and improved core materials are developed that allow for comparable biocompatibility.

Figure 2:
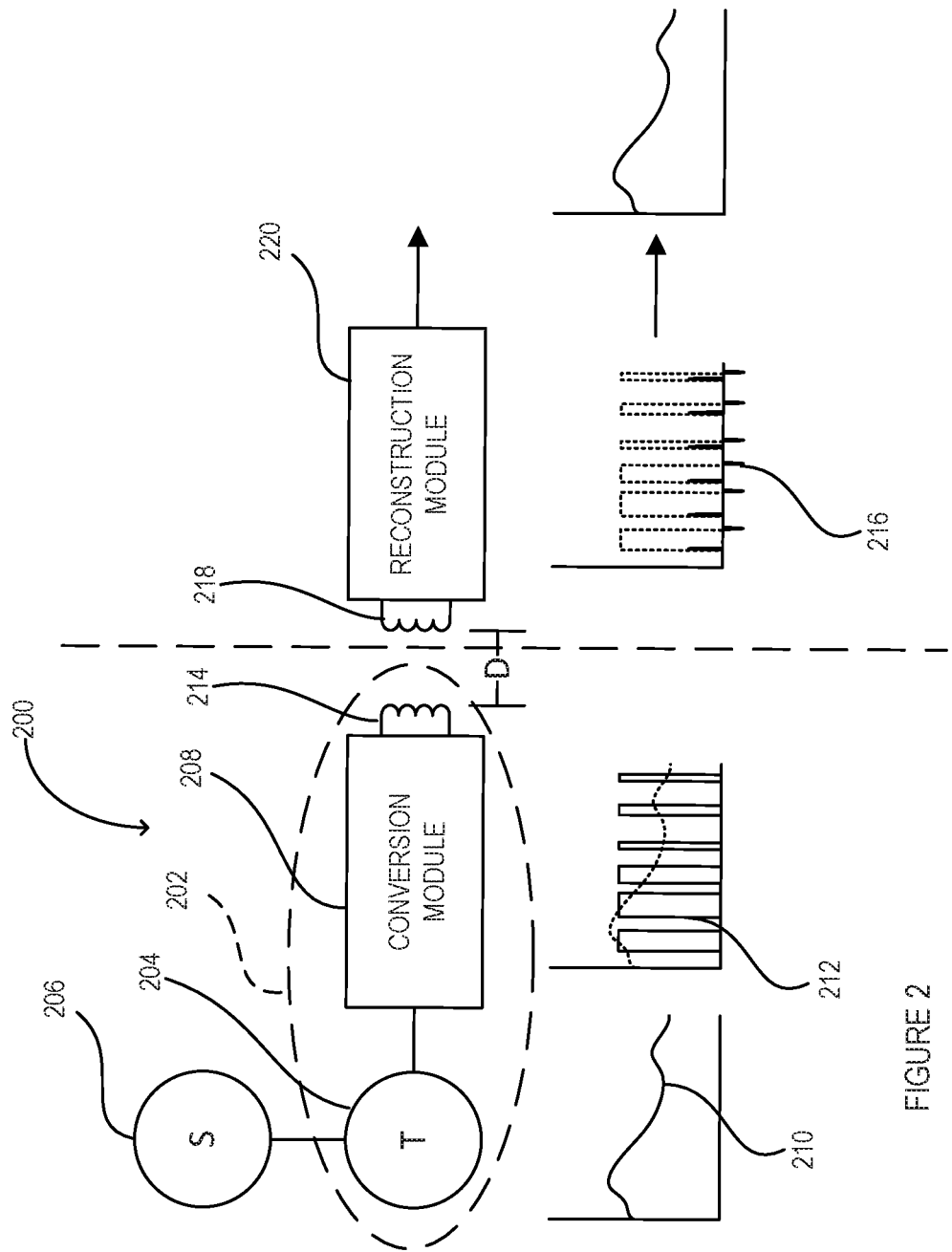
FIG. 2 is a schematic diagram of an implantable communication system, in accordance with another embodiment of the invention.

Referring now to FIG. 2, and in accordance with another embodiment of the invention, an alternative system 200 comprises an implantable signal communication device 202 having an integrated transducer 204 for operative coupling to a distinct sensing device 206 and operatively coupled to a conversion module 208, whereby sensing device 206 communicates a sensed characteristic to the transducer 204 to be converted thereby into a characteristic signal 210 appropriate for conversion by the conversion module into an inductively transmittable signal 212. As in the embodiment described above with reference to FIG. 1, the converted signal 212 is propagated through implantable inductor 214, which induces a corresponding signal 216 through external inductor 218, allowing for external reconstruction of the characteristic signal via reconstruction module 220.

Figure 3:
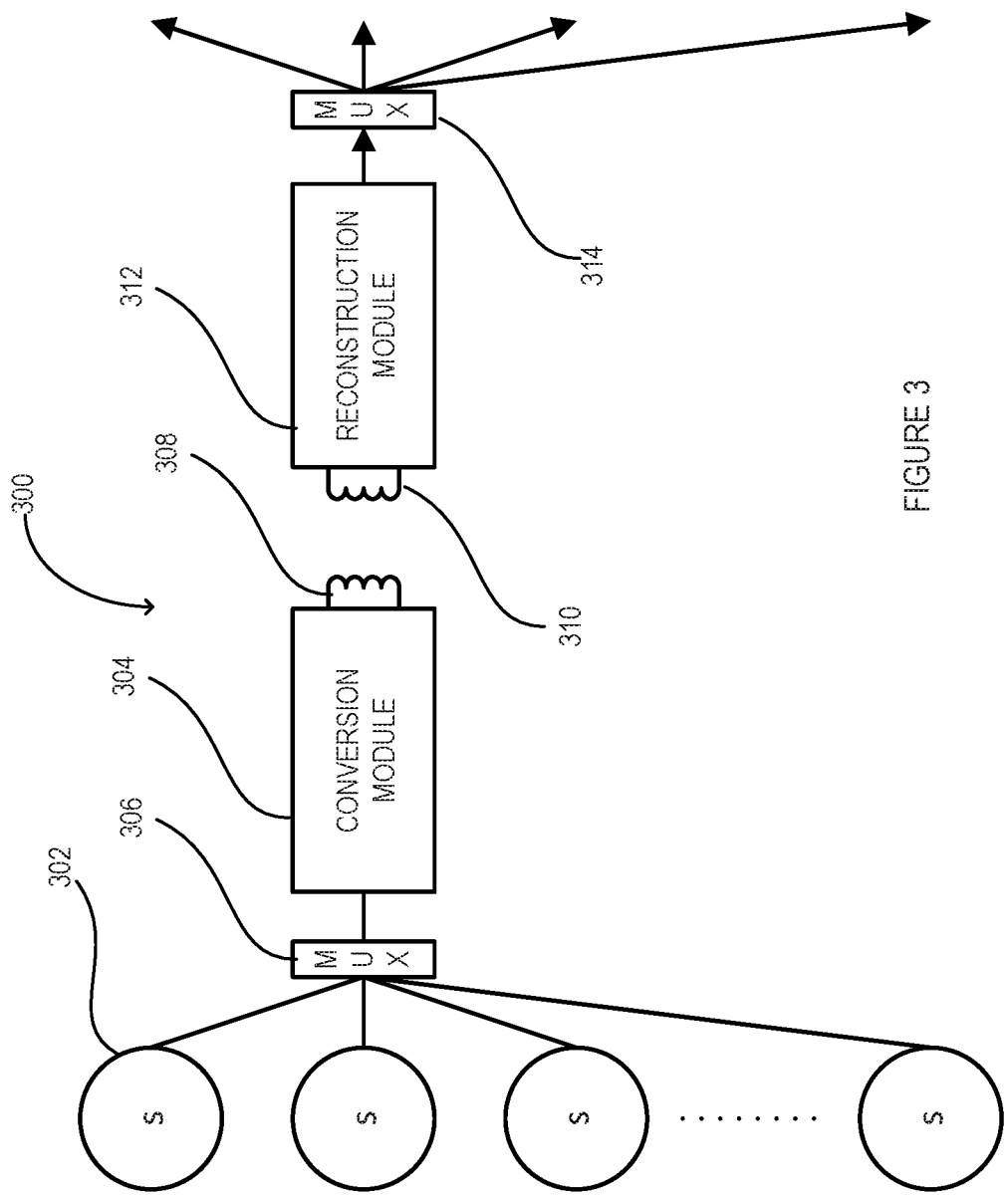
FIG. 3 is a schematic diagram of an implantable communication system for use with multiple sensing devices, in accordance with another embodiment of the invention.

Referring now to FIG. 3 and in accordance with another embodiment of the invention, an alternative system 300 is depicted, wherein multiple sensing devices 302 are communicatively linked to a same implantable conversion module 304 via a multiplexer (MUX) 306 or the like. In this embodiment, each of the sensing devices 302 is adapted to communicate a characteristic signal through the multiplexer 306 to the conversion module 304, wherein each characteristic signal may represent a same or distinct internal characteristic of the body within which they are implanted. For example, an array of identical sensing devices, or again a combination of similarly intended sensing devices (e.g. different types of devices adapted for a same or similar sensing purpose) may be used in combination to probe various locations within the body. Alternatively, or in addition thereto, a series of different sensing devices may be used to probe different characteristics of the body, whereby a combined assessment of such sensed characteristics may lead to a more comprehensive monitoring or diagnostic of the body's condition, state, etc. It will be appreciated that, while not explicitly depicted herein, different types of sensing devices may be operatively implemented via respective or common transducers for the acquisition and transmission of data representative of a variety of internal parameters.

As with the previously described embodiments, each intra-body signal communicated to the conversion module may be converted into an inductively transmittable signal, such that propagation thereof through implantable inductor 308 induces a corresponding signal in external inductor 310, which can be used to reconstruct each internally converted signal (e.g. via reconstruction module 312) and ultimately recover, via demultiplexer 314, each respective characteristic signal of interest.

In one embodiment, each characteristic signal is converted and transmitted sequentially, for example, by the sequential processing of each data signal for transmission over a single data channel. Namely, the system 300 may be configured to synchronize sequential transmissions from respective sensing devices in a prescribed order, whereby a processing platform (not shown but optionally encompassing demultiplexer 314) may be configured to recognize the order within which each signal is received and associate same with a mapping of associated sensing devices implanted within the body. While this provides one example of a multiplexing protocol, the person of ordinary skill in the art will appreciate that other time segregated transmission protocols may be implemented to implement sharing of a single data channel for multiple data signals. Alternatively, or in addition thereto, other multiplexing techniques may be utilized, for example encompassing distinct communication channels, provided system implementation techniques are respected to minimize cross-talk and/or interference between inductively transmitted channels.

Figure 4:
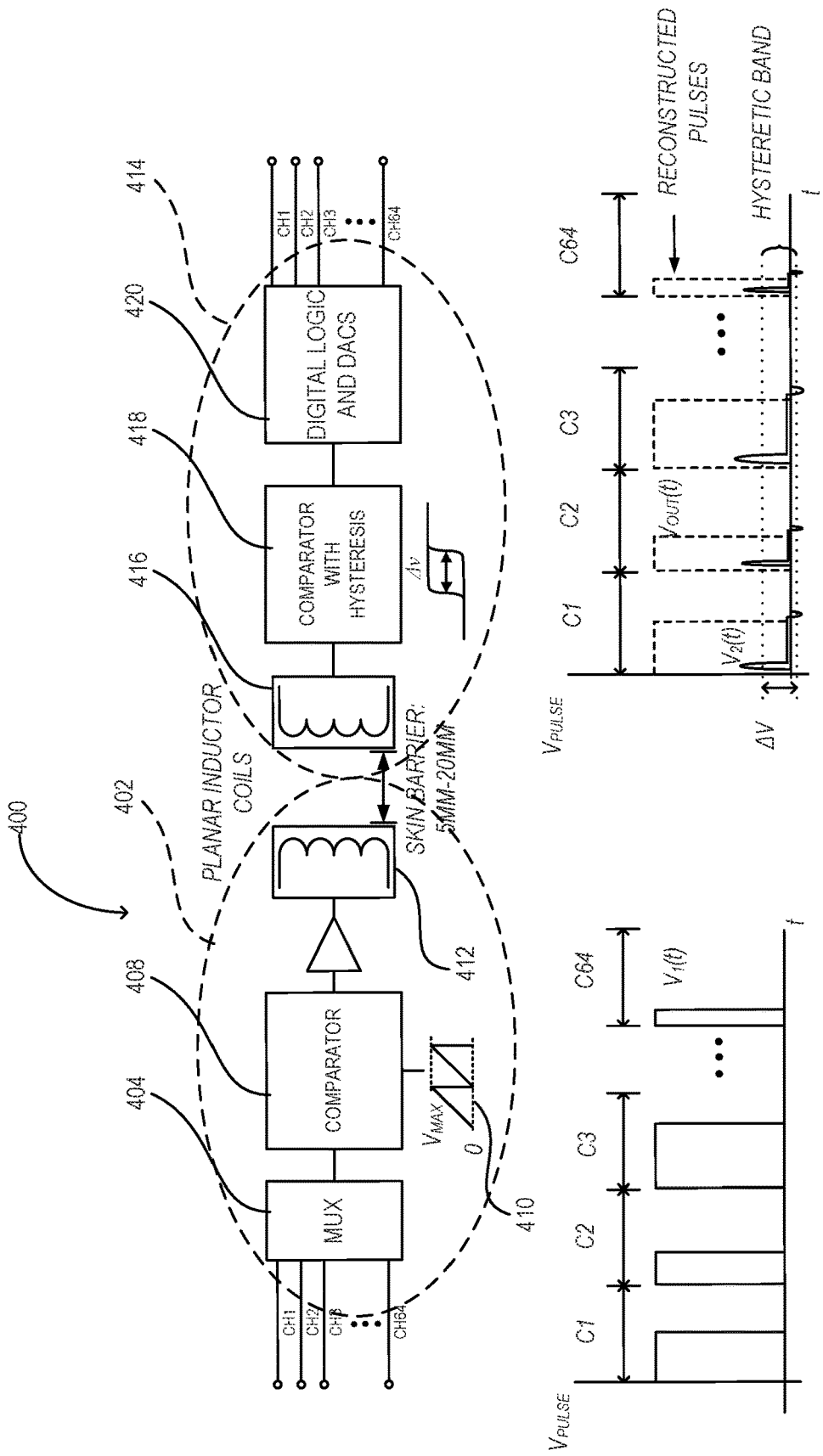
FIG. 4 is a schematic diagram of an implantable communication system showing further illustrative implementation detail, in accordance with another embodiment of the invention.

Referring now to FIG. 4, further detail is provided with respect to an exemplary embodiment of the invention, wherein 64 data channels are multiplexed for sequential transmission over a single inductively transmitted data channel. In this embodiment, the system 400 comprises an implantable device 402 operatively receiving as input via multiplexer 404, intra-body signals from 64 representative sensors (not shown). Each signal is illustratively multiplexed in sequential order for processing by a comparator 408 which receives as input the multiplexed data channel and a saw-tooth wave 410, resulting in the pulse-width-modulation of the multiplexed signal. The modulated signal is thus propagated through implantable inductor 412, a planar inductor coil in this example, to be inductively transmitted through the skin (e.g. distance of approximately 5-20 mm) for external processing by an external processing platform 414.

Namely, a corresponding signal is induced in an external inductor 416 of the external processing platform 414 (e.g. again depicted illustratively as a planar inductor coil). As contemplated by the above-described example, each rise and fall of the internally propagated PWM signal induces corresponding signal pulses in the external inductor. Feeding these inductively generated pulses in a comparator with hysteresis 418, for example, enables the external processing platform to substantially reconstruct the PWM signal and thereby recover and process the respective characteristic signals via, for example, appropriate analog-to-digital converters and digital logics 420.

It will be appreciated that the above details are provided as examples only and are in no way intended to limit the scope of the present disclosure. Namely, and as discussed above, different signal conversion/encoding approaches may be considered. Also, while this example applies data transfers through the skin, other communication distances may also be considered, for example, to provide for deeper implantation of sensing devices, or the like.

As shown by the accompanying schematic data signal charts of FIG. 4, data from each sensing device or subchannel is converted into respective representative PWM characteristic signals, illustrated within time slots C1 to C64 sequentially, in this example. This sequentially modulated signal is jointly referenced as $V_1(t)$ and effectively represents the characteristic signal to be inductively transmitted via implantable inductor 412. Correspondingly, signal pulses, depicted herein as $V_2(t)$, are sequentially induced through the external inductor 416. Upon applying upper and lower signal limits, e.g. via hysteretic band Δv, the internally generated PWM signal can be effectively reconstructed (e.g. each positive and negative pulse corresponding to a rise and fall, respectively, of the PWM signal) resulting in reconstructed signal $V_{OUT}(t)$. With application of appropriate logics, each data subchannel can be segregated for processing, as appropriate or desired.

Figure 5:
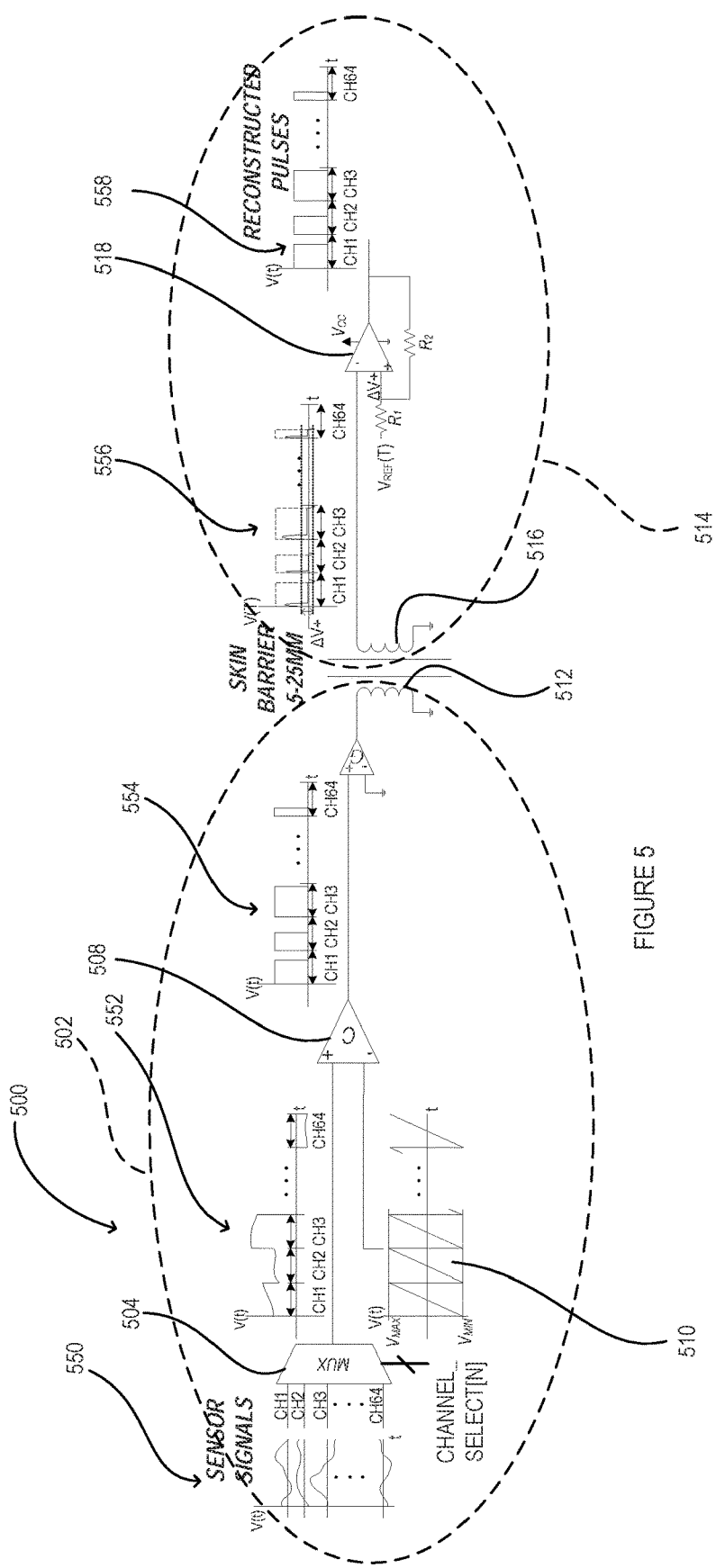
FIG. 5 is a schematic diagram of an implantable communication system showing further illustrative implementation detail, in accordance with another embodiment of the invention.

Referring now to FIG. 5, further detail is provided with respect to another exemplary embodiment of the invention, wherein 64 data channels are again multiplexed for sequential transmission over a single inductively transmitted data channel. In this embodiment, the system 500 comprises an implantable device 502 operatively receiving as input via multiplexer 504, intra-body signals from 64 representative sensors (not shown). Each signal is illustratively multiplexed in sequential order via multiplexer 504 for processing by a comparator 508 which receives as input the multiplexed data channel and a saw-tooth wave 510, resulting in the pulse-width-modulation of the multiplexed signal. The modulated signal is thus propagated through implantable inductor 512, to be inductively transmitted through the skin (e.g. distance of approximately 5-25 mm in this example) for external processing by an external processing platform 514. As will be appreciated by the skilled artisan, while the example provided in FIG. 4 contemplates a transmission distance through the skin of approximately 5-20 mm, as compared to 5-25 mm contemplated in the example provided in FIG. 5, greater distances may also be achievable within the present context without departing form the general scope and nature of the present disclosure. For example, by adjusting system performances and sensitivities, devices provided at greater implantation depths may also benefit from the communication protocols and techniques contemplated herein, and such considerations are thus intended to fall within the scope of the present disclosure.

A corresponding signal is induced in an external inductor 516 of the external processing platform 514. As contemplated by the above-described example, each rise and fall of the internally propagated PWM signal induces corresponding signal pulses in the external inductor. Feeding these inductively generated pulses in a comparator with hysteresis 518, for example, enables the external processing platform to substantially reconstruct the PWM signal.

As shown by the accompanying schematic data signal charts of FIG. 5, data (signals 550) from each sensing device or subchannel is sequentially multiplexed (multiplexed signal 552) and converted into respective representative PWM characteristic signals 554, illustrated within time slots C1 to C64 sequentially, in this example. This sequentially modulated signal 554 represents the characteristic signal to be inductively transmitted via implantable inductor 512. Correspondingly, signal pulses (signal 556) are sequentially induced through the external inductor 516. Upon applying upper and lower signal limits, e.g. via hysteretic band ΔV, the internally generated PWM signal can be effectively reconstructed (e.g. each positive and negative pulse corresponding to a rise and fall, respectively, of the PWM signal) resulting in reconstructed signal 558. With application of appropriate logics, each data subchannel can be segregated for processing, as appropriate or desired.

The following provides details as to an illustrative setup used, in accordance with one embodiment, in evaluating operative characteristics of the above-described embodiments. In particular, this setup was designed for the implementation of four (4) data channels, which, upon being sequentially multiplexed and modulated, were transferred and received as described above, over a distance similar to that expected for an implantable device. Materials used were also generally limited to implantable materials and/or technologies where such implantability may be of particular interest. In this particular test, the turns ratio between sending (implanted) and receiving (external) coils was 1:2, though it will be appreciated that this ratio may be adapted or reversed depending on the intended application, particularly should the device ultimately be used as a bi-directional device, which may include several coils, for example. In this example, the separation between tracks of the coils was roughly 0.8 mm. It will be appreciated however that other distances may be considered without departing from the general scope and nature of the present disclosure.

In this particular setup, the following operating sequence was implemented. As suggested by the above-described embodiments, but in no way intended as a limiting factor, the implanted multiplexor is configured to run through the channels at a sampling rate of several MHz. Each channel is then sequentially processed by the comparator for a certain window of time (e.g. dictated by selection signal to multiplexor) and compared with a ramp function at the same frequency. As will be appreciated by the person of ordinary skill in the art, this approach will generally generate one square pulse for each channel, in sequential order. Each pulse is then propagated, after amplification, to and through the implantable inductor, such as a coreless and/or planar inductor, whereby it is significantly attenuated. Despite such attenuation, the original square pulse signal may be substantially reconstructed by exploiting the respective peaks and valleys generated through the external inductor. Once reconstructed, the analog signal can be regenerated for further processing.

In accordance with another embodiment, rather than to cycle through all channels sequentially, a header in the form of a brief pre-signal pulse can be used to indicate which channel is being read. In order to optimize communications using this approach, however, the header would generally be of a much simpler format than that of traditional communication systems as, in order to integrate and implant a device, all discrete components generally need to be miniaturized and inductors generally need to be optimized to operate well under different possible conditions.

The embodiments of the invention contemplated herein and within the scope and context of the present disclosure provide for the effective wireless communication of intrabody signals and data via inductive coupling between an implantable device and an external receiver. Namely, while respecting constraints an limitations applied to implantable devices, such as bio-compatibility, avoidance or reduction of adverse biological effects (e.g. common with traditional inductive communication hardware such as cored inductors and the like), power consumption efficiency, etc., the embodiments of the invention herein described and contemplated provide for an attractive alternative to commercially available devices. Namely, in some embodiments, the proposed system may allow for external recording of up to, if not more than 64 signals, for example acquired via implanted ECoG, deep brain stimulation (DBS) or UTAH electrodes, or via other known electrodes such as microwire electrodes, single neuronal cell electrodes, electrodes for recording small populations of neuronal cells, nerve cuff electrodes, nerve penetrating electrodes, and/or other electrode types provided for neuronal recording, for example. Signals may also, or alternatively, be recorded via known biosensors and appropriate transducers of interest and/or via environmental sensors of interest, to name a few. In some embodiments, signals may be acquired at a sampling rate of anywhere from 1 kHz up to 15 kHz, or more, for example. As will be appreciated by the skilled artisan, other types of electrodes may also be considered. As depicted illustratively herein, the proposed system design allows for minimal processing logic within the body, and rather allows for most of the system's processing intelligence to be maintained externally, which not only allows for a reduction in implantable circuitry (and its associated drawbacks), but also allows for interoperability of the implanted device with different processing platforms, which may change based on progress in the field of intra-body signal processing, or again from one processing platform to the other. Effectively, as will be appreciated by the person of ordinary skill in the art, a versatile implantable communication device can be designed that is consistent with the teachings of the present disclosure for interoperable implementation with different types of sensing devices and external processing platforms, while implementing a substantially similar internal processing and transmission protocol in each implementation. Furthermore, as the raw signal can be effectively reconstructed for external processing, access to raw data and a full gamut of sensed information can be effectively extracted, which, using conventional devices, would generally impose a greater processing burden on the internal processing and transmission platform. Using certain embodiments of the invention, however, access to substantially raw data can be provided while maintaining roughly 40% or higher implantable device efficiency.

In accordance with another embodiment of the invention, the above-described approach to data communications can be applied generally to different contexts whereby data is to be transferred across a biological barrier, either from within the body to an external receiver, as described in the above examples, from outside the body to an internal receiver, or again, between an implantable transmitter/receiver pair. Namely, while the above examples provide certain advantages with respect to the provision of simplified implantable data transmission systems, similar advantages may also be leveraged in the implementation of such systems in the reverse direction, namely where data is to be communicated to an implantable receiver for processing and/or implementing one or more actions within the body.

Accordingly, in one example consistent with such embodiments, the system may comprise an encoder, which may be internal or external to the body, for generating an encoded signal defined by successive width-encoded pulses representative of the data, and a transmission inductor operatively coupled to the encoder for propagation therethrough of the encoded signal. The system may further comprise an implantable receiver comprising a receiving inductor for disposal at a distance through the biological barrier from the transmission inductor for operative magnetic coupling thereto, wherein each rise and fall of the successive width-encoded pulses induces corresponding signal pulses through the receiving inductor, for example as described above with respect to the embodiments of FIGS. 1 to 5, and shown in FIGS. 1, 2 and 4.

In this embodiment, the system further comprises an implantable data reconstruction module for reconstructing each rise and fall of the encoded signal from the corresponding signal pulses to recover the encoded signal. Accordingly, the recovered encoded signal could then be used internally to drive and/or implement one or more actions within the body, such as for example, via one or more implantable electrical stimulation electrodes, probes and the like.

For example, in one embodiment, the above-described system may be used to provide electrical stimulation to the brain, which stimulation may be encoded via the width encoded signal to mimic or replicate traditional brain impulses to induce a reaction in or provide an external signal to the patient, who may, for example, suffer from neurological and/or central nervous system damage/disorders, or again for use in the control and/or operation of prosthetic devices or the like, to name a few examples. For instance, in one embodiment, a pressure sensor could be carried on the finger of a patient to record a pressure exerted by the finger when grabbing an object, which pressure could then be converted into a standardized brain stimulus signal to be communicated to the patient's brain in allowing the patient to recognize this pressure. In this particular example, an appropriate brain stimulus signal may be represented by a series of signal spikes, the repetition frequency of which increasing with pressure (e.g. high frequency being correlated with a signal of higher importance for the brain to recognize and acknowledge). While the tactile sensor in this example would generally be carried externally (or as part of a prosthetic arm or hand), it may also be implanted within the finger of a patient having reduced sensory capabilities, in which case, this pressure signal could in fact be externalized via one of the embodiments described above. In either case, the signal thus constructed would need to be communicated to the brain.

Following from this example, the detected pressure could be adequately encoded for brain stimulation via a width-encoded pulsed signal, whereby the frequency of the signal could reflect the exerted pressure to be communicated to the brain (e.g. spike frequency), and where the width of each respective pulse could represent an intended stimulation area of the brain (i.e. broader pulses would trigger a greater surface area of the brain as compared to narrower pulses by transferring, for a given or preset signal amplitude, a higher charge to the brain). As will be appreciated by the skilled artisan, other stimulation parameters could also or alternatively be encoded in this manner.

Upon propagating this pulse width-encoded signal through a transmitting inductor, as described above, which may be external or internal to the patient's body but generally at a distance across a biological barrier from an implanted receiving inductor, pulses corresponding to each rise and fall of the pulse width-encoded signal will be manifested through the implanted receiving inductor, from which the pulse width-encoded signal can be reconstructed and directly applied to stimulate the brain via one or more aptly positioned electrodes. For example, in one embodiment, an effective signal amplitude may be previously encoded within the implantable signal reconstruction module such that, upon detecting the pulses generated through the receiving inductor and corresponding to each rise and fall of the transmitted signal, the width of each pulse and their frequency may be reconstructed and applied at the preset signal amplitude to stimulate the brain. It will be appreciated that the receiving inductor may be implanted in a vicinity of the stimulation electrode, for example, or again provided at a significant distance therefrom and linked thereto via appropriate wiring or the like. These and other such permutations will be readily apparent to the skilled artisan.

In other examples, the system may be used for the communication of control parameters and/or commands to an implantable device. For example, an externally generated command may be communicated via the above-described communication system to an actuator of the implantable device to achieve a desired effect or action. Examples of such implantable devices may include, but are not meant to be limited to an artificial muscle, a pump for drug delivery, a retinal stimulator for stimulating visual sensation, and other such devices, as will be readily appreciated by the skilled artisan.

As will be appreciated by the skilled artisan, the relatively simplified communication protocol considered above and applied herein can provide significant advantages in the provision of an effective communication system for transferring data across a biological barrier. Furthermore, as discussed above, given the high data transfer frequencies available using the above-described embodiments, multiple data channels may be communicated concurrently via a single data stream, whereby sequential channel allocations may be utilized at high frequencies to provide accurate data across the biological barrier for multiple channels while limiting transfer protocol complexities common with traditional communication protocols.

As will be further appreciated by the skilled artisan, while the above example is limited to the communication of pressure-related information, the embodiments of the invention herein considered are not to be limited as such and may in fact be utilized for the transfer of different biological and/or environmental data/information across different biological barriers, and that, from within the body to an external receiver, from outside the body to an implantable receiver, or again between an implantable transmitter/receiver pair. Exemplary applications may include, but are not limited to, deep brain stimulation systems (e.g. for closed-loop control of deep brain stimulators using sensors external to the body for the treatment of Parkinson's disease), brain monitoring and recording systems (e.g. for long term monitoring of epileptic patients), brain machine interfaces (e.g. for control of prosthetic arms, neuroprosthetic systems and assistive devices), electromyography (EMG) recordings (e.g. for control of prosthetic arms, neuroprosthetic systems and other assistive devices), blinking prostheses, and cochlear implants (e.g. fully or partially implanted), to name a few. These and other such considerations should now be readily apparent to the person of ordinary skill in the art, and are therefore meant to fall within the scope of the present disclosure.

A further advantage applicable in at least some of the above examples, and other embodiments of the invention, is provided by the potentially significant reductions in power consumption achievable. For example, using current communication protocols, an internal signal is sampled and its amplitude represented by a string of 1 and 0 bits, which bits are then sent wirelessly as distinct frequencies that are received and decoded back into 1 and 0 bits. In order for the receiving end to establish the incoming frequency, at the very least, several pulses for each bit are needed. Further, the more accurate the amplitude recovery, the more bits are needed. This multiplicative effect results in many pulses being sent for a given sample. In comparison, and in accordance with some embodiments, intra-body signal amplitude may be encoded by the width of a single pulse, which can be recovered on the receiving end to reconstruct the original pulse and recover the sampled value. In accordance with some embodiments, this may allow for a several fold decrease in the number of pulses transmitted for communicating a given quantum of data, which can translate in a corresponding decrease in overall power consumption, and thus have positive consequences in operating time and overall system simplifications, all of which being of particular relevance for implantable applications.

Further to potential power consumption reductions, since a sampled intra-body signal amplitude may be encoded and communicated, in accordance with one embodiment, via a single pulse (as opposed to tens of pulses in current designs), the same sampling time may be used to sample more channels, and/or to acquire further samples on a given channel. Overall, this may translate into more channels being monitored, and/or the effective monitoring of faster moving signals than could have otherwise been reconstructed. Accordingly, using different embodiments of the invention herein described may allow overcoming certain limitations in the detection and/or reconstructions of certain intra-body signals, and/or in expanding data transmission capabilities for different wireless applications, particularly short or close range applications.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A system for communicating data across a biological barrier, the system comprising:
    an implantable device suitable for implantation in a body and comprising a sensing device for generating a characteristic signal representative of an internal characteristic of the body, a signal conversion module operatively coupled to said sensing device for converting said characteristic signal into an encoded signal defined by successive width-encoded pulses representative of said characteristic signal, wherein each width-encoded pulse comprises a substantially square wave signal having a rise, a substantially constant value, and a fall, and an implantable inductor operatively coupled to said signal conversion module for propagation therethrough of said encoded signal,
    wherein each said rise and fall in said encoded signal is defined to induce a corresponding positive pulse and negative pulse, respectively, on an external inductor for external reconstruction, and the substantially constant value of each width-encoded pulse being of a width that causes the induced positive and negative pulses to be separated by a flat zero signal.

2. The system of claim 1, wherein said implantable inductor comprises a coreless inductive coil.

3. The system of claim 1, wherein said implantable sensing device comprises an implantable lead for sensing electrical impulses in the body.

4. The system of claim 1, wherein the body is a human body and wherein said implantable sensing device is encapsulated for implantation in the human body.

5. The system of claim 4, wherein said implantable device comprises a subcutaneous or hypodermic device, and wherein said external receiving device is configured for disposal on the skin, said distance being defined by implantation depth through skin.

6. The system of claim 1, wherein said external inductor comprises an inductive coil.

7. The system of claim 1, said implantable device comprising two or more implantable sensing devices for generating respective characteristic signals.

8. The system of claim 7, wherein said conversion module is configured to sequentially propagate, through the successive width-encoded pulses, respective encoded signals of said characteristic signals of the two or more implantable sensing devices.

9. The system of claim 8, comprising at least 4, 8, 16, 32 or 64 data channels, characteristic signals generated in respect of each one of which being converted by said conversion module for said sequential propagation through said implantable inductor for said external reconstruction.

10. The system of claim 8, said two or more implantable sensing devices comprising two or more types of sensing devices for generating respective characteristic signals representative of distinct internal characteristics of the body.

11. The system of claim 8, further comprising a multiplexer configured to receive the respective characteristic signals from the two or more implantable sensing devices and for outputting a selected characteristic signal to said conversion module.

12. The system of claim 1, wherein said conversion module applies a pulse-width-modulation (PWM) to said characteristic signal in converting said characteristic signal into said encoded signal.

13. The system of claim 1, wherein said sensing device comprises one or more of the following electrodes: electrocorticography (ECoG) electrodes, deep brain stimulation (DBS) electrodes, microwire electrodes, single neuronal cell electrodes, electrodes for recording small populations of neuronal cells, multielectrode array (MEA) electrodes, nerve cuff electrodes, or nerve penetrating electrodes.

14. The system of claim 1, wherein said sensing device comprises a transducer for converting a sensed internal characteristic into an electric characteristic signal representative thereof to be converted by said conversion module.

15. The system of claim 14, wherein said sensing device comprises one or more blood pressure sensor, body temperature sensor, blood oxygen saturation (SpO2) sensor, blood CO2 saturation sensor, NO concentration sensor, or respiration sensor.

16. The system of claim 1, wherein said sensing device comprises one or more environmental sensors.

17. The system of claim 1, wherein a respective width of each width-encoded pulse is representative of the internal characteristic of the body.

* * * * *